(12) United States Patent
Brown (10) Patent No.: US 7,666,156 B2
(45) Date of Patent: Feb. 23, 2010

(54) KNEE BRACE AND METHODS OF USE AND MODIFICATION THEREOF

(76) Inventor: Alice M. Brown, 7600 Madeline St., Saginaw, MI (US) 48609-4991

( * ) Notice: Subject to any disclaimer, the term of this patent is extended or adjusted under 35 U.S.C. 154(b) by 95 days.

(21) Appl. No.: 11/466,639

(22) Filed: Aug. 23, 2006

(65) Prior Publication Data

US 2007/0185423 A1    Aug. 9, 2007

Related U.S. Application Data

(60) Provisional application No. 60/771,062, filed on Feb. 7, 2006.

(51) Int. Cl.
*A61F 5/00* (2006.01)
*A61F 13/00* (2006.01)
*A61F 13/06* (2006.01)
*A41D 13/00* (2006.01)

(52) U.S. Cl. .................... 602/23; 602/1; 602/5; 602/26; 128/889; 128/892; 2/22; 2/24; 2/62

(58) Field of Classification Search ............. 602/1, 602/5, 23, 26; 128/889, 892; 2/22, 24, 62
See application file for complete search history.

(56) References Cited

U.S. PATENT DOCUMENTS

| 4,275,716 A | * | 6/1981 | Scott, Jr. ................ 602/26 |
| 4,353,362 A | | 10/1982 | DeMarco |
| 5,248,292 A | * | 9/1993 | Holland .................. 602/6 |
| 5,451,201 A | * | 9/1995 | Prengler ................. 602/26 |
| 5,656,023 A | | 8/1997 | Caprio, Jr. et al. |
| 5,865,776 A | | 2/1999 | Springs |
| 5,873,848 A | | 2/1999 | Fulkerson |
| 6,336,909 B2 | | 1/2002 | Gildersleeve et al. |
| 6,402,712 B1 | * | 6/2002 | Gauvry ................... 602/26 |
| 6,773,411 B1 | | 8/2004 | Alvarez |
| 2002/0010410 A1 | * | 1/2002 | Steponovich ........... 602/26 |
| 2003/0069530 A1 | * | 4/2003 | Satou et al. ............. 602/75 |
| 2004/0225245 A1 | * | 11/2004 | Nelson ................... 602/26 |
| 2005/0240134 A1 | | 10/2005 | Brown |

OTHER PUBLICATIONS

Patellofemoral Foundation Website, www.patellofemoral.org.

(Continued)

*Primary Examiner*—Patricia M Bianco
*Assistant Examiner*—Tarla R Patel
(74) *Attorney, Agent, or Firm*—Robert L. Stearns; Dickinson Wright, PLLC (57) ABSTRACT

A knee brace, method of use thereof, and modification to an existing knee brace facilitates inducing side loads to a knee joint to align upper and lower leg portions relative to one another, thereby allowing the knee joint to function properly over its full dynamic range of motion. The knee brace, whether as manufactured or modified, acts to apply a lateral shear force to the knee joint through application of opposing lateral forces, with one lateral force being above the knee joint in one direction and the other lateral force being below the knee joint in an opposite direction. The counteracting forces act to shift femoral condyles and tibial condyles of the knee joint back into proper lateral alignment without acting directly on the patella to counteract the effects of the patella femoral syndrome.

5 Claims, 9 Drawing Sheets

OTHER PUBLICATIONS

Donjoy Website, www.donjoy.com.
S.E.R.F. Strap Patellofemoral Brace Ad, Copyright dj Orthopedics, LLC.
DME-Direct Website, www.dme-direct.com.
Scott A. Paluska, MD, Douglas B. McKeag, MD, MS, "Using Patellofemoral Braces for Anterior Knee Pain", The Physician and Sportsmedicine, vol. 27, No. 8—Aug. 1999.
Patellofemoral Braces, Knee Pain Info Website, www.kneepaininfo.com.
Frank G. Shellock, PhD, FACSM, Michael Mullin, ATC, PTA, Kevin R. Stone, MD, Mark Coleman, RT(R)ARRT, John V. Crues, MD, Kinematic Magnetic Resonance Imaging of the Effect of Bracing on Patellar Position: Qualitative Assessment Using an Extremity Magnetic Resonance System, Journal of Athletic Training, vol. 35, No. 1, Mar. 2000.

* cited by examiner

KNEE BRACE AND METHODS OF USE AND MODIFICATION THEREOF

CROSS-REFERENCE TO CO-PENDING APPLICATION

This patent application claims priority to U.S. Provisional Patent Application Ser. No. 60/771,062, filed Feb. 7, 2006, which is hereby incorporated herein by reference in its entirety.

BACKGROUND OF THE INVENTION

1. Technical Field

This invention relates generally to knee braces, and more particularly to knee braces worn externally about a knee joint for supporting and manipulating the knee joint.

2. Related Art

Figure 1:
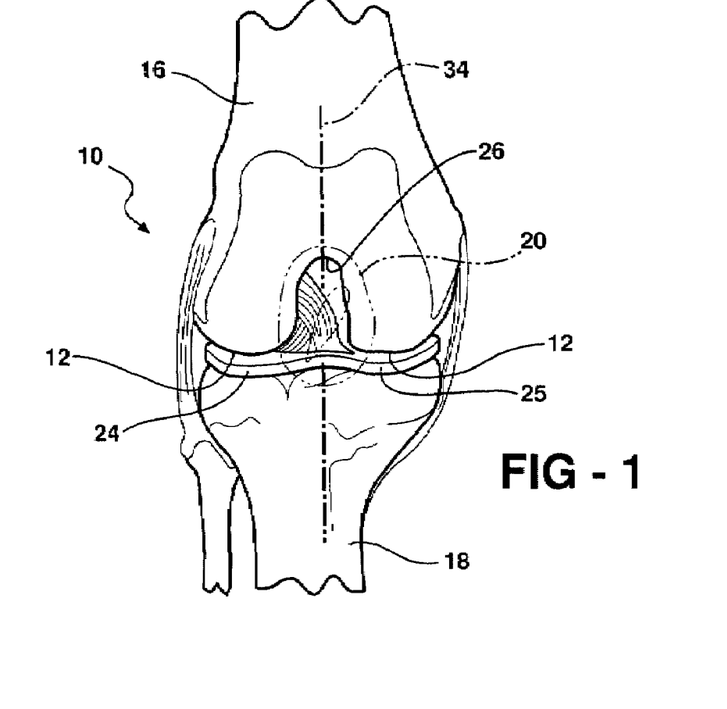
FIG. 1 is a schematic front view of a human knee joint with the tibia and femur shown properly aligned.
Figure 2:
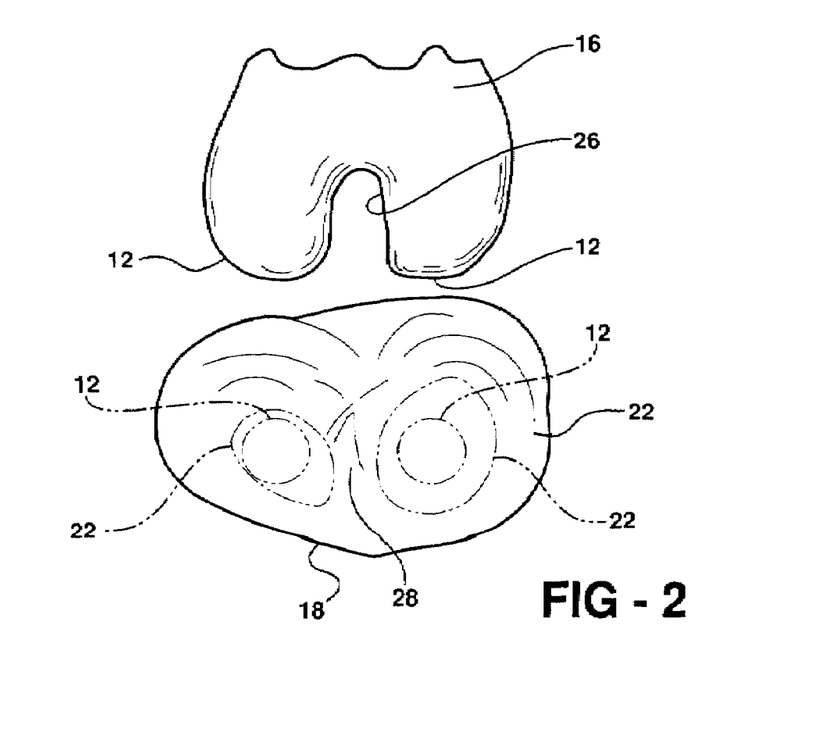
FIG. 2 is an exploded partial plan view of the knee joint looking down on the tibia and illustrated in the proper alignment position of the femur for a normal joint condition.

As is known, and shown in FIGS. 1 and 2, a knee joint 10 is the largest joint in the body and has a unique anatomy due to its unusual movement. Though it may appear to the casual observer as a simple joint, in actuality, it is extremely complex. The complexity results from the fact that the knee joint 10 has femoral condyles 12 that rotate downward and slightly medial with each flexion of a lower leg portion, then rotate slightly backward and upward with the extension of a lower leg portion 14 relative to an upper leg portion 15. Accordingly, the rotation of the knee joint results in a three-dimensional movement, rather than a two-dimensional movement seen in more simple joints, such as an elbow, for example.

The knee joint 10 is made up of three bones which interact with one another to provide the three dimensional movement of the joint. One of the bones is the largest bone in the body, the femur 16, which supports the upper leg portion 15 and is commonly referred to as the thighbone. Two others are the tibia 18, which is commonly referred to as the shinbone, and the patella 20, which is commonly referred to as the kneecap. In addition to the femur 16, the and tibia 18 has ends referred to as condyles, each of which are bifurcated into lateral and medial condyles 22. The femoral condyles 12 and the tibial condyles 22 are separated from direct frictional engagement with one another by separate layers of cartilage, commonly referred to as the lateral and medial meniscus 24, 25. Each meniscus 24, 25 is generally C-shaped, and fits into the joint between the femoral condyles 12 and the tibial condyles 22 to facilitate rotating and sliding movement therebetween. To further facilitate proper movement and reduce friction within the knee joint 10, a synovium tissue, which produces synovial fluid, lubricates the joint. Of course, the knee joint 10 includes many tendons and ligaments to produce the movement of the knee, and to stabilize its alignment, some of which are discussed hereafter.

The femoral condyles 12 are generally quite rounded and are bifurcated to form an inverted V-shape groove 26 traversing anterior and posterior sides of the knee. The respective tibial condyles 22 are generally somewhat less rounded, and produce what is commonly referred to as the tibial plateau. The tibial plateau also has a small V-shaped groove 28 traversing the anterior and posterior sides of the knee in generally mirrored relation to the groove 26 in the femur 16. The middle portion of the tibial plateau has a slight up cropping on which anterior (ACL) and posterior (PCL) cruciate ligaments attach. The cruciate ligaments stabilize the knee front to back.

The medial meniscus 25 (on the inside portion of the knee) and the lateral meniscus 24 (on the outside portion of the knee) are in the shape of cartilage rings which circumvent the edges of the tibial condyles 22 to create a cushion for the tibial plateau. The rings define generally convex receptacles for receipt of the rounded femoral condyles 12 throughout their range of motion. Preferably, the femoral condyles 12 are maintained in a generally snug fit within the receptacles to prevent slop or wobbling of the femoral condyles 12 relative to the tibial receptacles. Accordingly, in a properly functioning knee joint, the femur 16 articulates relative to the tibia 18 in a smooth and stable motion.

Figure 5:
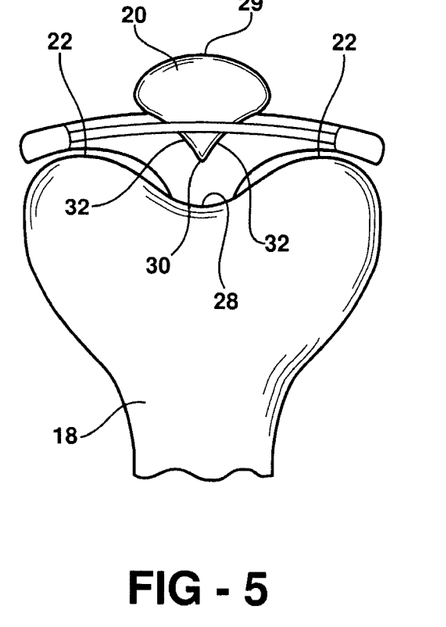
FIGS. 5 and 6 are schematic of the knee joint illustrating the respective proper and improper tracking of the patella relative to the tibia plateau for a normal knee and one afflicted with patello-femoral syndrome.

The patella 20 functions to tension the knee joint 10 throughout its range of motion, as well as to protect the joint from impact forces. The patella 20 is maintained in position to follow a slight deviation medially and laterally while remaining within in the V-shaped grooves 26, 28 between the femoral and tibial condyles 12, 22. Proper alignment of the patella 20 during articulation of the knee joint 10 prevents damage to the tibial condyles 22 and the separate meniscus 24, 25 as it tracks across them. The patella 20 also tracks with a slight rotation in its upward and downward movements. The patella 20 fits into the inverted V-shaped groove 26 of the femur 16 and tracks over the smaller frontal V-shaped groove 28 of the tibia 18 (FIG. 5). The shape of the patella 20 is roughly that of an inverted pear, which is rounded and smooth on an outer surface 29, and providing a generally V-shaped projection 30 on an underside to define laterally spaced, generally concave portions 32 which track over the femoral condyles 12. The precise shape of the patella 20 and the underside projection 30 and curvatures 32 varies from person to person. In some people, the projection 30 is generally pronounced and in others it is more subtle. It is believed that people having a more pronounced and sharp projection 30 on the underside of the patella 20 encounter more problems with tracking of the patella 20 during articulation of the knee joint 10.

The knee joint 10 is designed to withstand generally large forces vertically, typically up to 400 pounds or more, however, it is not designed to withstand significant side forces, whether originating laterally or medially. With normal usage, the knee joint 10 will generally last a lifetime, yet one-quarter million Americans require knee replacement surgery every year. Accordingly, something out of the ordinary generally must happen to the knee joint 10 for it to require medical attention, such as surgical repair or replacement.

Figure 3:
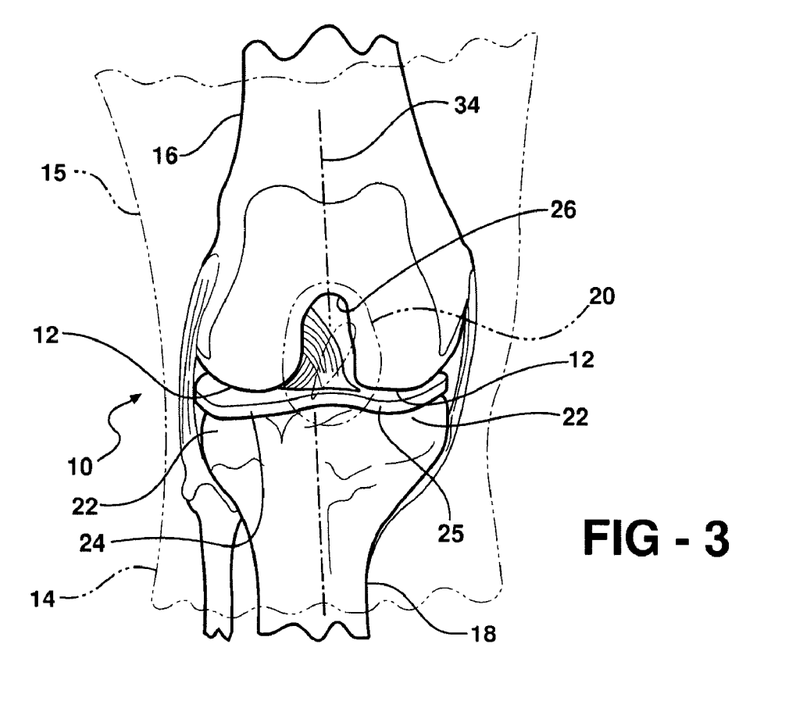
FIGS. 3 and 4 correspond to FIGS. 1 and 2, respectively, however, show the knee joint with patella femoral syndrome resulting from misalignment of the femur and tibia across the knee joint.
Figure 4:
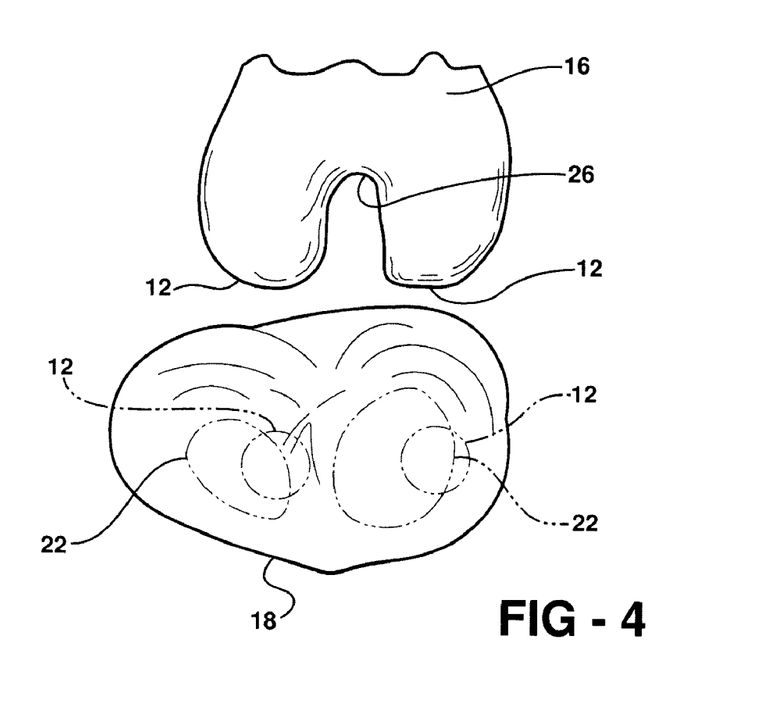
Figure 6:
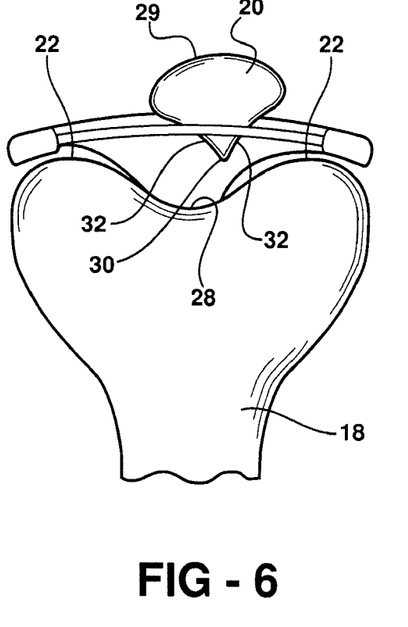

Unfortunately, the high degree of mobility of the knee joint 10 means it is more susceptible to being shifted off its midline plane 34 either laterally or more commonly, medially. This condition is commonly known as patello-femoral syndrome (FIGS. 3, 4 and 6). Once the knee joint 10 is shifted off the mid-plane 34, an individual's body weight, in addition to increased vertical compression loads generated in use, generates a side or shear load due to the misalignment. The shear load results in laterally opposite loads that are not desirable for normal operation of the knee joint 10. This new, skewed force vector will continue to create additional shear forces throughout the knee joint 10 with each and every flexion, thus, further skewing the shear force vector angle from its normal vertical direction. Eventually, the shear forces cause accelerated wear to the aforementioned components of the knee joint 10, and create a degree of slack in the affected medial and lateral tendons such that they are no longer able to maintain the femur 16 and tibia 18 in their proper stable alignment relative to the midplane 34. As a result, the patella 20 is no longer able to track in the V-shaped grooves 26, 28 between the femoral and tibial condyles 12, 22 during flexion of the knee joint 10, thereby leading to collateral damage.

When the femur 16 and tibia 18 are not correctly aligned, or if the meniscus 24, 25 is damaged, the femoral condyles 12 do not fit properly into the cavities of the meniscus 24, 25. In turn, this can cause the patella 20 to continually track improperly directly over the meniscus 24, 25 instead of through the V-shaped groove 28 of the tibial plateau. A relatively minor lateral shift of the patella 20 can decrease the surface contact area by 60%, and consequently increase the shear forces by 2½ times, depending on the sharpness or degree of the protrusion 30 on the underside of the patella 20 and the angle at which the protrusion 30 comes down on the meniscus 24, 25.

If the misalignment of the patella 20 is bad enough, the meniscus 24, 25 can be cut by the protrusion 30 to create a flap, wherein the flap can interfere with the flexion of the knee joint 10, and in some cases, get pinched during flexion, thereby causing extreme pain. Eventually, continued wear can result in shredding of the meniscus 24, 25, which can result in the meniscus 24, 25 being unable to contain the femoral condyles 12. Accordingly, once off track, the patella 20 can further irritate or injure the cartilage covering the condyles 12, 22, in addition to tearing or shredding the meniscus 24, 25. Any irritation or injury will initiate a typical body response of inflammation, pain and swelling. If this condition persists, the body may then mount an anti-inflammatory response to destroy or cordon off the inflamed tissue, thereby forming chondromalacia under the knee cap 20, more swelling and more fluid. This begins a vicious cycle in which the knee cartilage can be destroyed, and if left unchecked, the bones can be damaged.

Surgical intervention may be necessary to remove the flap of meniscus 24, 25 or to smooth out the shredded meniscus surface and to scrape off chondromalacia from the underside of the patella 20. Accordingly, the procedure generally reduces the size of the meniscus wall, thereby reducing the ability of the menisci 24, 25 to contain the femoral condyles 12 throughout a full range of motion of the knee joint 10. In addition, scraping the underside of the patella 20 can result in further irritation, and thus, can eventually result in more chondromalacia being formed. As a result, eventually, the knee joint 10 may need to be replaced.

The above-described condition of patello-femoral syndrome is commonly diagnosed by elimination. This is because the condition requires only a very small degree of misalignment of the femoral and tibial condyles 12, 22, the menisci 24, 25 and the tendons of the adjacent muscles. These changes are not normally detectable by MRI, CT scan, X-Ray or other non-invasive means. Yet, even a small correction of the misalignment back toward the proper alignment of the Q-angle, defined as the angle between the patellar tendon and the quadriceps, has an unexpectedly great decrease on the effects of the patello-femoral condition, and thus, a great decrease in the pain caused by misalignment.

Patello-femoral syndrome can be identified by knee arthroscopy, which is an invasive procedure. Arthroscopy can show chondromalacia of the patella 20, fluid in the knee capsule, cyst in the knee joint 10, and if great enough, both fluid and cysts may also be shown by MRI. Further, shredding and/or tearing of the menisci 24, 25 covering the tibial condyles 22 cannot be seen.

In an attempt to correct the small degree of misalignment in a knee joint 10, traditional knee braces are often used under a misconception that they are effective in correcting a patello-femoral condition. However, traditional knee braces are generally not effective in correcting the misalignment condition, or in lessening the pain associated therewith, since they typically apply equal and circumferentially uniform pressure on and around the knee joint 10 and the adjacent portions of both the lower and upper leg portions 14, 15. Some traditional braces have hinges to limit flexion of the knee joint 10 in bending and raising the lower leg portion 14, and also help to prevent side-to-side motion of the knee joint 10. Other knee braces have rigid side bars to further limit the range of motion of the knee joint 10 from side-to-side. Although these knee braces can be effective in restricting movement of the knee joint 10, they are largely ineffective in correcting a patello-femoral condition due to their application of equal and circumferentially uniform forces about the knee joint 10, and to their inability to realign misaligned femoral and tibial condyles.

Most of the less expensive knee braces are sleeve-type, which are generally both difficult to put on and uncomfortable after continued use. In addition, sleeve-type braces made of neoprene inhibit heat dissipation and restrict the flow of blood to and from the knee joint 10, and thus, often result in swelling and pain. Some of the sleeve-type braces include hinges to support the knee joint 10 along the medial and lateral sides, but they limit the natural side-to-side rotation of the femur 16 during flexion. This limited side-to-side movement can prevent the knee joint 10 from making a complete recovery from damage, thereby preventing it from returning to its normal range of motion. This can result in further complications by allowing the muscles to be trained to move the knee joint 10 in an unnatural motion. In addition, rigid side bar braces also prevent normal rotation of the femur 16 present in its normal 3-D path of movement, and thus, do not allow natural tracking of the knee joint 10. Accordingly, they can also be ineffective in correcting a patello-femoral syndrome condition.

To overcome the difficulties of putting on sleeve-type braces, wrap-around knee braces are commonly used. The wrap around knee braces presently available also apply equal and circumferentially uniform pressures on and around the knee joint 10, and thus, are equally ineffective in treating a patello-femoral syndrome condition. In known wrap-type knee braces, straps above and below the knee joint 10 extend from the same side of the knee brace and are wrapped around the leg in the same circumferential direction. This contributes to the effect of placing equally directed pull forces above and below the knee joint 10. Wrap-around knee braces that have a main body portion of the brace behind or posterior to the knee joint 10 primarily support the upper and lower portion of the tendons attached to the patella 20. As such, these function to stabilize the pulley action of the patella 20, and may allow some rotation of the femur 16, but also result in an unnatural motion of the patella 20 by restricting its range of movement. In addition, they do not affect the realignment of the femoral or the tibial condyles 12, 22. As mentioned, if the femoral and the tibial condyles 12, 22 are misaligned, even slightly, the patella 20 cannot track correctly, and it will eventually damage the cartilage, menisci and synovial tissue that covers the adjacent surfaces of the bones which move over each other during flexion of the knee joint 10.

Another known wrap around knee brace construction is shown in U.S. Pat. No. 5,873,848, in which three separate straps are used to impart a side force directly on the patella to realign the knee joint. One strap is first fastened above the knee joint, then another is fastened below the knee joint, while a third strap is fastened to the first and second straps, with the third strap engaging the patella to cause its realignment. Not only is this a complicated mechanism to apply, but it also attempts to correct a patello-femoral syndrome condition by applying a side force directly on the patella. Though this may provide temporary relief to symptoms associated with the patello-femoral syndrome condition, it is not believed to be the best way to correct the source of the problem associated with the condition, which is misalignment of the femoral condyles relative to the meniscus and tibial condyles, and not misalignment of the patella.

A knee brace constructed in accordance with the present invention overcomes or greatly minimizes any limitations of the knee braces described above, thereby allowing a knee-joint experiencing a patello-femoral syndrome condition to be properly realigned via a knee brace that is easily applied, wherein the knee brace does not directly act on the patella. As such, a knee brace in accordance with the invention prevents or reduces collateral damage to the knee joint, and possibly negates the necessity for invasive surgical procedures to correct the damaged knee joint, while also providing a most effective recovery of the damaged knee joint.

SUMMARY OF THE INVENTION

A knee brace constructed according to one aspect of the invention is designed to be mounted on the leg of a user to induce a side-load to correct a patello-femoral syndrome condition in a knee joint by constantly urging femur and tibia bones of the knee joint into proper alignment with one another. The side-load is applied such that it does not act on a patella of the knee joint, and thus, the petalla is able to seek its natural and proper location for tracking during flexion of the knee joint. Accordingly, the knee brace is effective in applying an oppositely directed lateral load above the knee joint, while simultaneously applying a medial load below the knee joint, or vise versa, as necessary to correct the patello-femoral syndrome condition.

According to a particular aspect of the invention, the knee brace has a main body portion with opposite sides extending between an upper portion and a lower portion. A first upper strap extends from one of the sides of the upper portion and has a free end for operable communication with the other side of the upper portion to establish one of the side loads. A first lower strap extends from the other of the sides of the lower portion opposite the first upper strap and has a free end for operable communication with the one side of the lower portion to establish the other of the side loads. As such, the knee brace effectively places the knee joint under a constant shear or side load, with one of the femur or tibia being biased laterally outwardly and the other of the femur or tibia being biased medially inwardly, relative to the unbraced condition of the knee joint. In a further aspect of the invention, the amount and intensity of the bracing, and thus, applied loads, can be readily adjusted to best accommodate the present condition of the knee joint in order to correct the patello-femoral syndrome condition to bring the knee joint into proper alignment.

Another aspect of the invention includes a method of correcting a patello-femoral syndrome in a knee joint of a leg by realigning femoral condyles of a femur in an upper leg portion above the knee joint with tibial condyles of a tibia in a lower leg portion below the knee joint through the application of a knee brace. The method includes the steps of: applying a side force in one direction on the upper leg portion with the knee brace by attaching the knee brace on an upper portion of the leg, and at the same time, applying another side force in a direction opposite the one direction on the lower leg portion by attaching the knee brace on the leg below the knee joint. Upon disposing the knee brace on the leg, the brace applies a continual counteracting side load to the knee joint to return the femur and tibia in proper alignment with one another, thereby allowing proper tracking of the patella. In one embodiment, disposing the knee brace on the leg includes fastening one side load applying strap above the knee joint without imparting a force directly on the patella to produce a side load in one of the lateral or medial directions, and fastening another side load applying strap below the knee joint without imparting a force directly on the patella to produce a side load in a direction opposite the strap above the knee joint. Further steps may include adjusting the knee brace to apply as much or as little counteracting side loading as necessary by adjusting the tension of the straps. As such, over time, as the knee joint begins to recover, the upper and lower load applying straps of the knee brace can be loosened, as less and less side load will be required to realign the femur relative to the tibia. As such, the knee brace has the advantage of relieving the pain normally associated with patello-femoral syndrome without undergoing an expensive and invasive procedure, with the ultimate goal being to eliminate the need for the knee brace once the muscles and tendons are strong enough to support the knee joint in proper alignment to enable proper tracking of the patella.

Yet another aspect of the invention includes a method of modifying an existing knee brace to correct a knee joint having misaligned femoral and tibial condyles. The unmodified knee brace has an upper portion for disposal on an upper leg portion above a knee joint and a lower portion for disposal on a lower leg portion below the knee joint. The method of modifying the knee brace includes the steps of: attaching a generally rigid member to one side of one of said upper or lower portions of the knee brace and leaving a side opposite the one side of the upper or lower portion free from modification. The rigid member acts to induce a side load spaced from the patella on the respective upper or lower leg portion, thereby bringing it into proper alignment with the other leg portion. As such, the knee joint, and particularly the patella, is able to track properly during flexion of the knee joint. Of course, as mentioned above, the ultimate goal is to eliminate the need for the knee brace once the muscles and tendons are strong enough to support the knee joint in proper alignment to enable proper tracking of the patella.

BRIEF DESCRIPTION OF THE DRAWINGS

These and other features and advantages of this invention will become more readily apparent to those skilled in the art upon review of the detailed description of presently preferred embodiments and best mode, appended claims and accompanying drawings, in which:

DETAILED DESCRIPTION OF PREFERRED EMBODIMENTS

Figure 7:
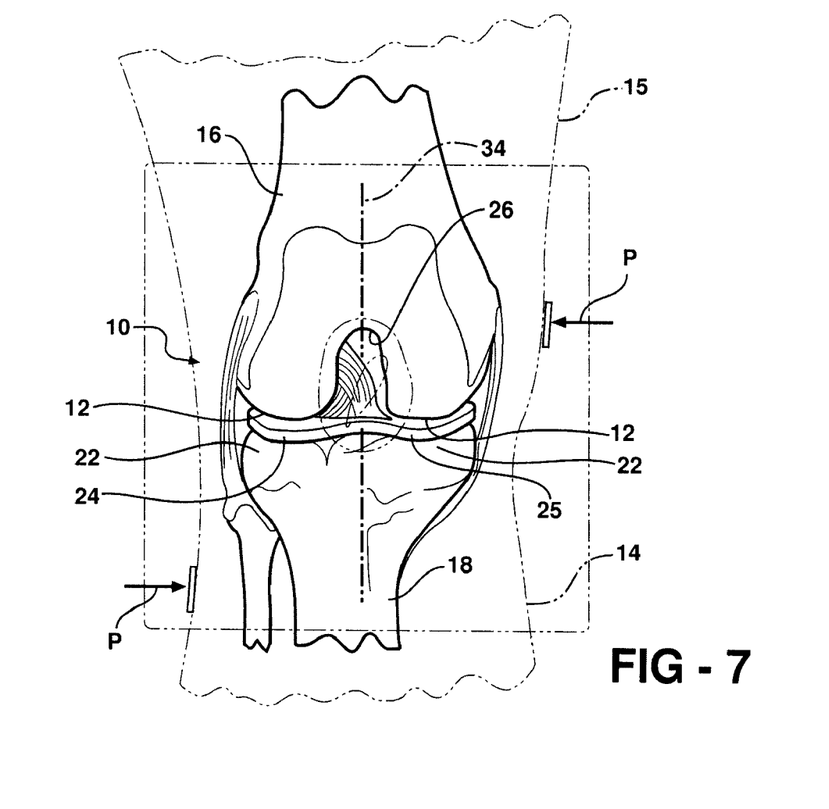
FIG. 7 schematically illustrates correction of the patello-femoral condition through application of a knee brace constructed in accordance with one presently preferred embodiment of the invention to the misaligned knee joint which imparts a corrective shear force to counteract and realign the patello-femoral knee joint to a normal condition.
Figures 8, 9A, 9B, 9C:
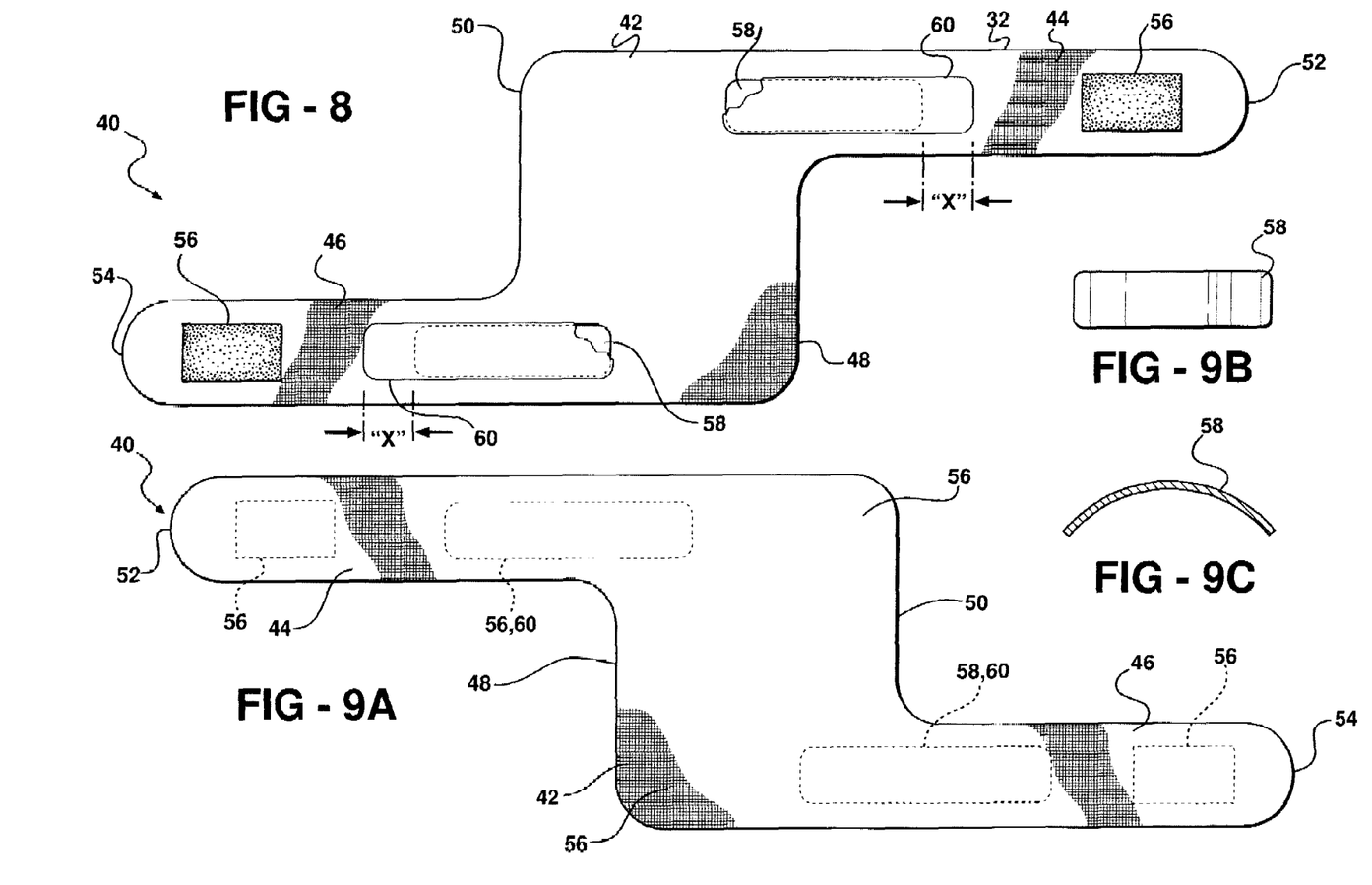
FIG. 8 is a back plan view of a knee brace constructed according to a first embodiment of the invention.
FIG. 9A is a top plan view of the knee brace of FIG. 8.
FIGS. 9B and 9C are plan and cross-sectional views respectively, of a stay incorporated in one embodiment of the knee brace.
Figure 10:
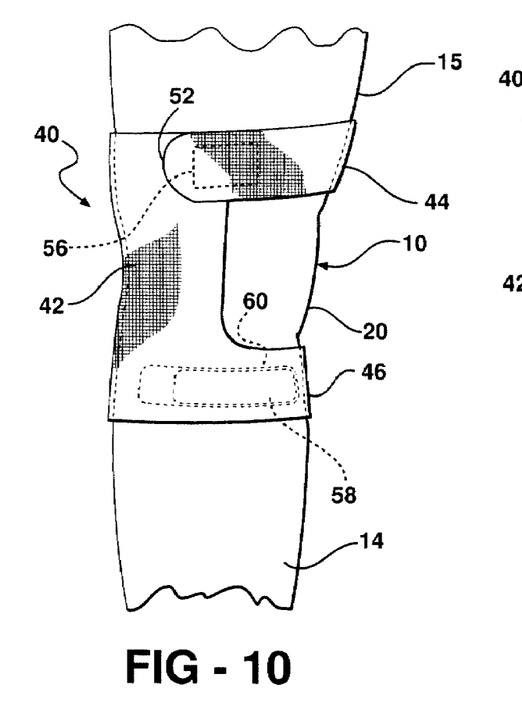
FIGS. 10 and 11 illustrate the knee brace of FIGS. 8 and 9 attached to the leg of a person as viewed from the lateral and medial sides, respectively.
Figure 11:
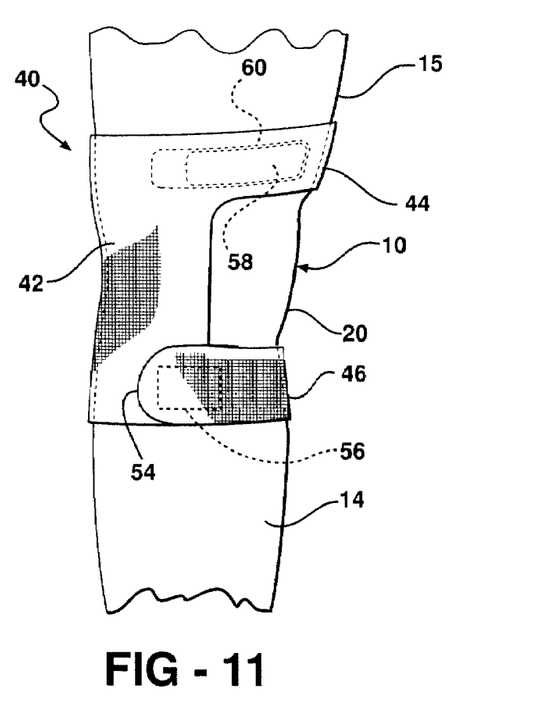
Figure 12:
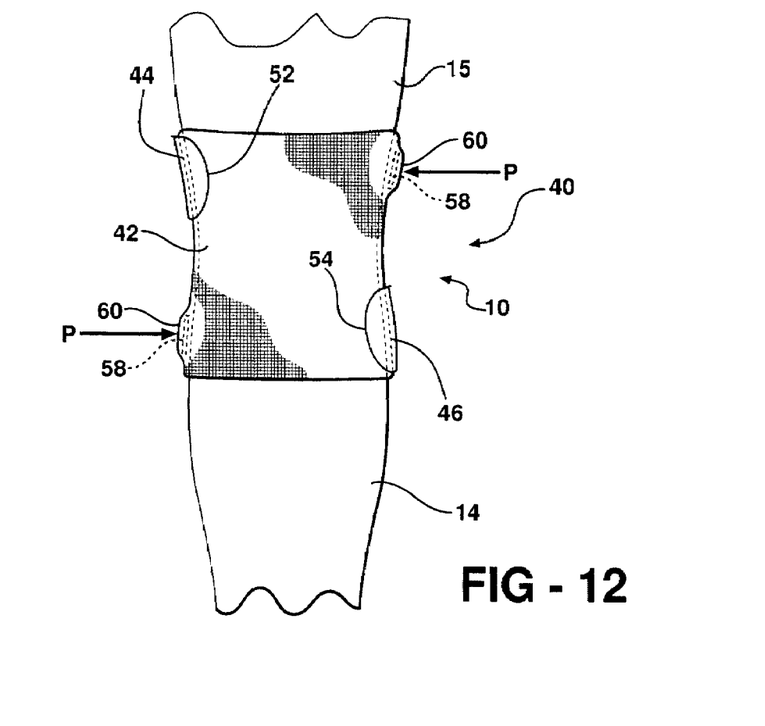
FIG. 12 is a view of the brace of FIGS. 8 and 9 shown attached to the leg from the back side of the leg.

Referring in more detail to the drawings, FIGS. 8-12 show a four-way knee brace 40 constructed according to one embodiment of the invention for imparting corrective shear or side loads resulting in corresponding side pressures above and below the knee joint 10 of a user. The knee brace 40 is adjustable to apply the appropriate magnitude of side forces in the respective lateral and medial directions above and below the knee joint 10 simultaneously to correct a condition of patello-femoral syndrome. The side forces applied opposite one another above and below the knee joint 10 realign the misaligned femoral and tibial condyles 12, 22 relative to one another, and in proper alignment with the meniscus 24 (FIG. 7) therebetween. Accordingly, the knee brace 40 relieves any discomfort typically associated with the patello-femoral condition, while also preventing potential or additional damage to the knee joint 10. As such, the knee brace 40 provides a noninvasive, economical mechanism to remedy a condition of patello-femoral syndrome, with the end goal being to eliminate the need for the knee brace 40 once the muscles and tendons are strong enough to support the knee joint 10 in its proper alignment.

As stated above, the four-way knee brace 10 is designed to treat patello-femoral syndrome by applying opposing forces resulting in pressures P (FIGS. 7 and 12) to the lower and upper leg portions 14, 15 in a manner so that the upper leg portion 15 is biased or directed in one direction, while the lower leg portion 14 is biased or directed in an opposite direction. Since only a small force is typically required to move the femoral and tibial condyles 12, 22 out of relative alignment, it stands to reason that a small force and resulting pressure P is required to bias or push/pull them back into proper relative alignment. Both the femoral and tibial condyles 12, 22 must realign for the patella 20 to track correctly in the respective V-shaped grooves 26, 28 between them. Application of the knee brace 40 to the injured knee joint 10 corrects the shear pressures off midplane 34 and the misalignment of the femoral and tibial condyles 12, 22, and thus, the pain associated with the condition is either reduced or totally eliminated with extension and flexion of the lower leg portion 14. Once the misalignment is corrected, continued wearing of the brace 40 will maintain the femur 16 and tibia 18 in proper alignment and help to strengthen and retrain the associated leg muscles to fire in correct alignment. Therefore, the muscles will no longer pull the patella 20, femur 16 and tibia 18 off track. Accordingly, it is believed that the knee brace applies a torque to the underlying musculature, which results in the muscles being repositioned in their proper orientation and trained to flex the upper and lower leg portions in proper alignment with one another. It should be recognized that all the embodiments of knee braces 40 discussed hereafter, constructed in accordance with the invention, apply generally equal and opposite pressures above and below the knee joint 10 to more correctly align the lower and upper leg portions 14, 15 to allow the patella 20 to glide superior and posterior, to rotate and to tilt sideways with the femoral and tibial condyles 12, 22, and to track correctly through the full, normal range of motion of the knee joint 10.

The knee brace 40 has a main body portion 42 with a first upper strap 44 and a first lower strap 46 extending from opposite sides 48, 50 of the body 42 in opposing directions to one another. The upper strap 44 extends from an upper portion of the main body portion 42 and from the side 48 and the lower strap 46 extends from a lower portion of the main body portion 42 and from the opposite side 50. The straps 44, 46 are preferably formed as one piece with the main body portion 42 and terminate at free ends 52, 54 adapted for operable communication with the main body portion 42. The straps 44, 46 are flexible such that the free ends 52, 54 can be wrapped for direct attachment to the respective upper and lower portions of the main body portion 42. Preferably, the free ends 52, 54 are equipped with one of a hook portion or loop portion of a hook and loop type closure 56, e.g., VELCRO®, while the main body portion 42 is equipped with the other hook or loop portion, thereby facilitating quick and easy attachment and adjustment of the free ends 52, 54 relative to the main body portion 42. However, it should be recognized that any suitable means for fastening the free ends 52, 54 to the main body portion 42 could be used, such as snaps, clasps or ties, for example.

The main body portion 42 of the brace 40 is intended to be positioned behind the leg, generally opposite the patella 20, wherein the upper strap 44 of the brace 40 is wrapped around the front of the upper leg portion 15 and above the patella 20, such that it is spaced from the patella, for attachment of the free end 52 back on the main body portion 42 generally behind the leg. The lower strap 46 of the brace 40 is wrapped in an opposite circumferential direction than the upper strap 44 around the front of the lower leg portion 14 and below the patella 20, such that it is spaced from the patella, for attachment of the free end 54 back on the main body portion 42.

The knee brace 40 can be equipped with generally rigid members, referred to hereafter as stays 58, positioned along the side of the femur 16 on one side of the leg and the side of the tibia 16 on an opposite side of the leg. The stays 58 can be attached to the brace 40 in any suitable fashion, however, to facilitate locating the stays 58 on the brace 40, pockets 60 can be formed at least partially on the straps 44, 46, and preferably on an inner side of the straps 44, 46, for receipt of the stays 58. To facilitate adjustment of the stays 58, the pockets 60 are preferably longer than the stays 58, such as by a predetermined dimension "X", which could be as much as 1-2 inches or more, as necessary to provide space to allow for minor positional adjustments of the stays 58 within the pockets 60.

Figures 21, 22A:
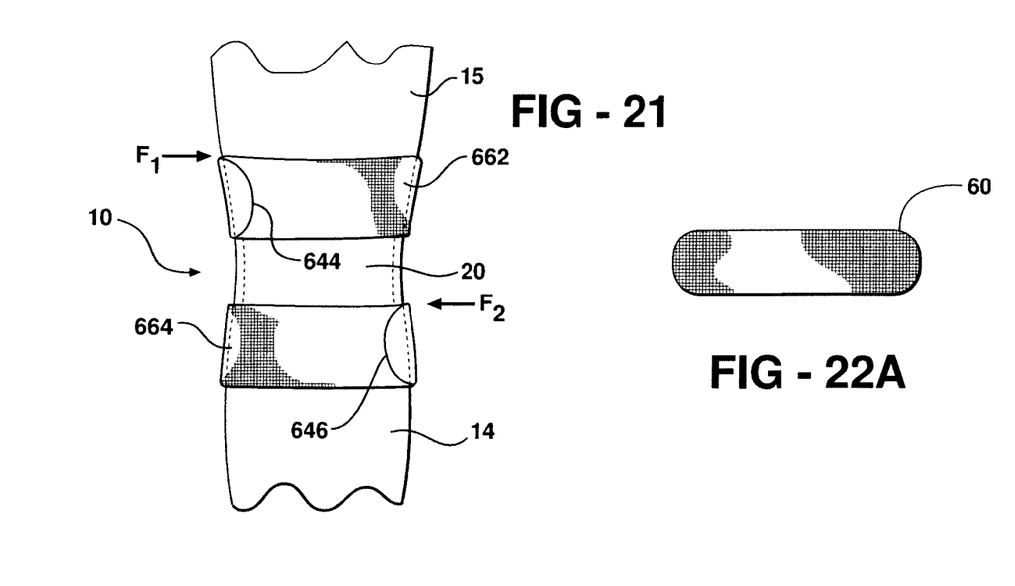
FIG. 21 is a front view of the brace of FIG. 20 shown in position on a user's leg.
FIGS. 22A-B illustrates a removable pocket that may be releaseably attached to various knee braces to enable the knee braces to impart a shear force across the knee joint with one force being applied above the knee in one lateral direction and the other force being applied below the knee in a medial direction, or vise versa, without applying a force directly on the patella, to correct misalignment between the upper and lower leg portions in accordance with the invention.
Figure 22B:
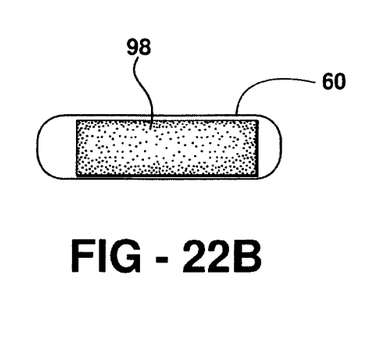

As such, the stays 58 can be positioned within the pockets 60 to adjust the direction of the applied force for maximum benefit and comfort. As shown in FIGS. 22A and 22B, the pockets 60 can be attached as separate features via a hook and loop fastening arrangement, or otherwise, wherein hooks 98 are shown on the pockets 60 for direct attachment to loop features on the fabric of the brace.

The stays 58, and thus the pockets 60, can be positioned partly on the main body portion 42 of the brace 40 and partly on the respective strap 44, 46 to apply opposing pressures to both the respective upper and lower leg portions 15, 14. As such, the upper stay 58 can apply pressure from the medial side of the knee joint 10 toward the lateral side of the knee joint 10 above the knee, and the lower stay 58 can apply an opposing pressure from the lateral side of the knee joint 10 toward the medial side of the knee joint 10 below the knee, thereby realigning the knee joint 10 and leaving the femoral and tibial condyles 12, 22 free to track correctly through a complete range of motion of the knee joint 10. It should be recognized that the knee brace 40 can be provided to apply forces in directions opposite to those described above. In addition, if better for correction of the injured knee, only one stay 58 can be used, usually laterally on the lower leg portion 14, to push it medially, although, the arrangement of the single stay 58 could be reversed. Accordingly, the stay 58 can be inserted or removed as necessary to obtain the best feel throughout healing and movement of the leg. Further, the stays 58 can be provided in various degrees of rigidity, from being very stiff, to being more pliable, thereby providing additional options throughout the healing process.

Once the main body portion 42 of the brace 40 is correctly positioned behind the knee, the straps 44, 46 can be adjusted as necessary to reduce or eliminate the patello-femoral condition. Further, the straps 44, 46 can be adjusted throughout the day as necessary. It should be recognized the brace 40 is applicable for both the left and right knee.

A knee brace 40 constructed according to another embodiment of the invention is shown in FIGS. 13-16. The knee brace 40 is similar to the embodiment shown in FIGS. 8-12, except for the provision of two additional shorter second upper and lower straps 62, 64 extending from opposite sides of the main body portion 42 from the respective longer upper and lower straps 44, 46 from the previous embodiment. The second upper and lower straps 62, 64 are free from any rigid members, and thus, remain flexible along their length to facilitate attachment to the respective first upper and lower straps 42, 46. Accordingly, the second upper and lower straps 62, 64 do not induce countering/canceling forces to the opposite forces induced by the longer first upper and lower straps 42, 46. Otherwise, the knee brace 40 is constructed the same and functions the same.

Figure 17:
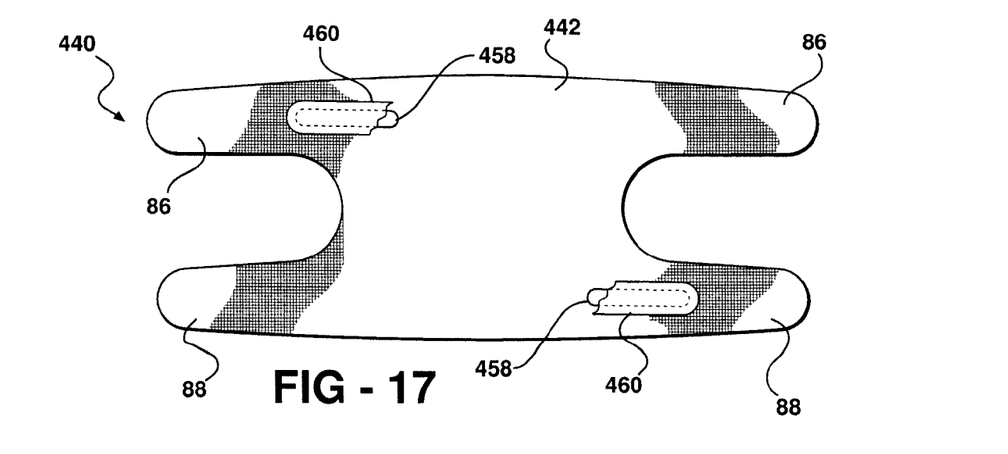
FIGS. 17-19 illustrate knee braces modified according to the invention.
Figure 18:
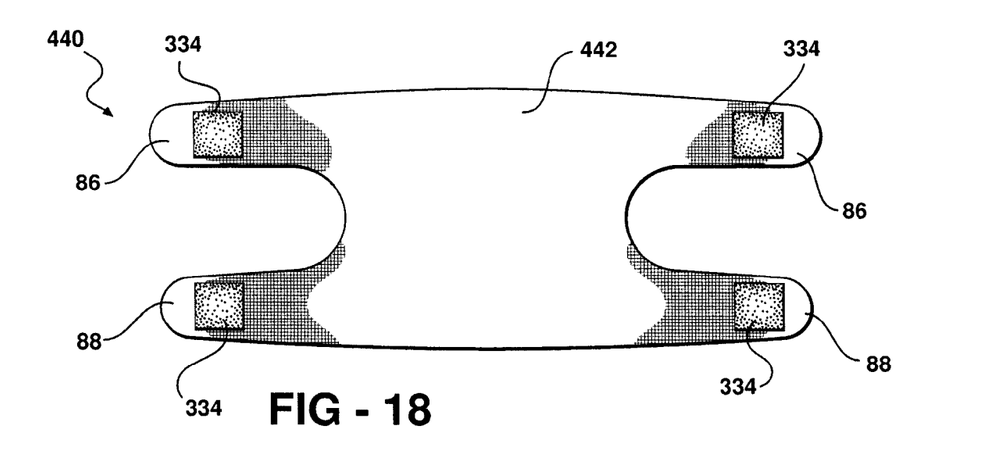
Figure 19:
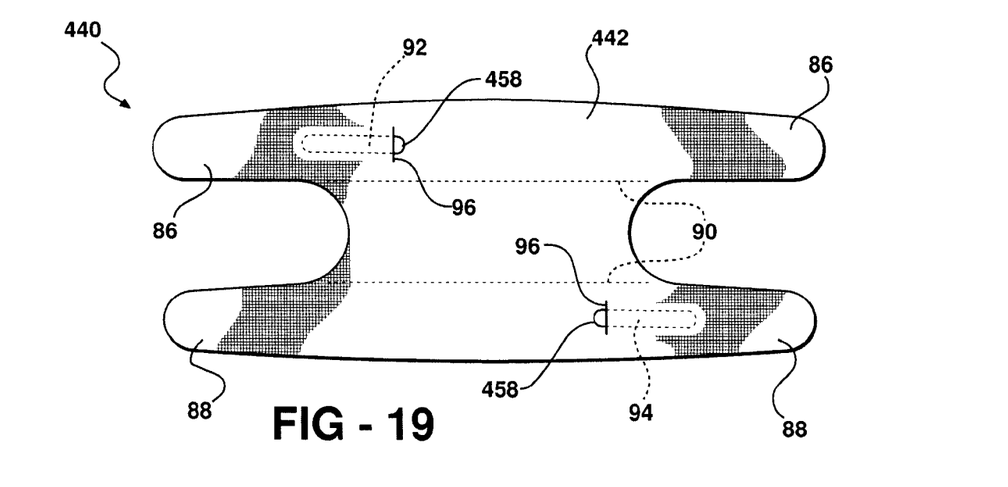

As shown in FIGS. 17-19, in accordance with another aspect of the invention, modification of a knee brace 440 having VELCRO® straps 86, 88 that wrap around the front upper and lower leg portions 15, 14, with a main body portion 442 of the brace wrapped around the back, without imparting direct forces on the patella, can correct a knee joint with patello-femoral syndrome. A stay 458 can be affixed partially on the main body portion 442, preferably in a pocket 460 similar or the same as those described above. The stay 458 is partially located on the straps 86, 88, one above the knee and one below the knee, spaced from the patella, on opposite sides of the respective upper and lower leg portions 15, 14. If the brace 440 is constructed from two layers of material, such as neoprene, sewn together at the edges (FIG. 27), a pair of horizontal stitch lines 90 can be sewn laterally across the brace 440 from the points of attachment of the straps 86, 88, top and bottom, to form upper and lower enclosed pockets or channels 92, 94, respectively, for receipt of the stays. A small slit 96 is then made through the back of the brace 440 for insertion of the stay 458 into the desired location of the enclosed channel.

Figure 13:
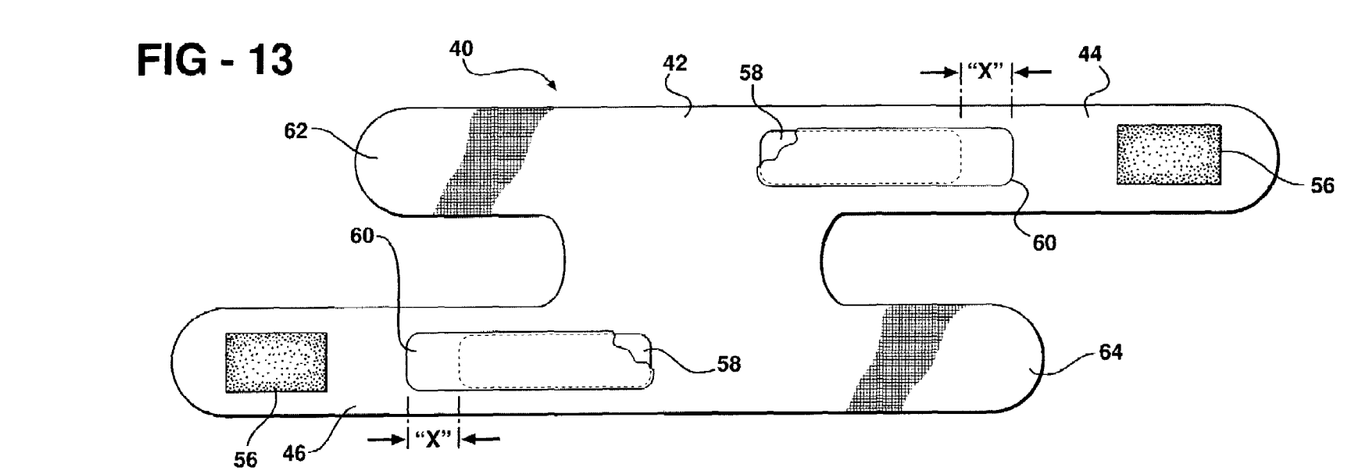
FIGS. 13 and 14 are respective back and front plan views of a knee brace according to a second embodiment of the invention.
Figure 14:
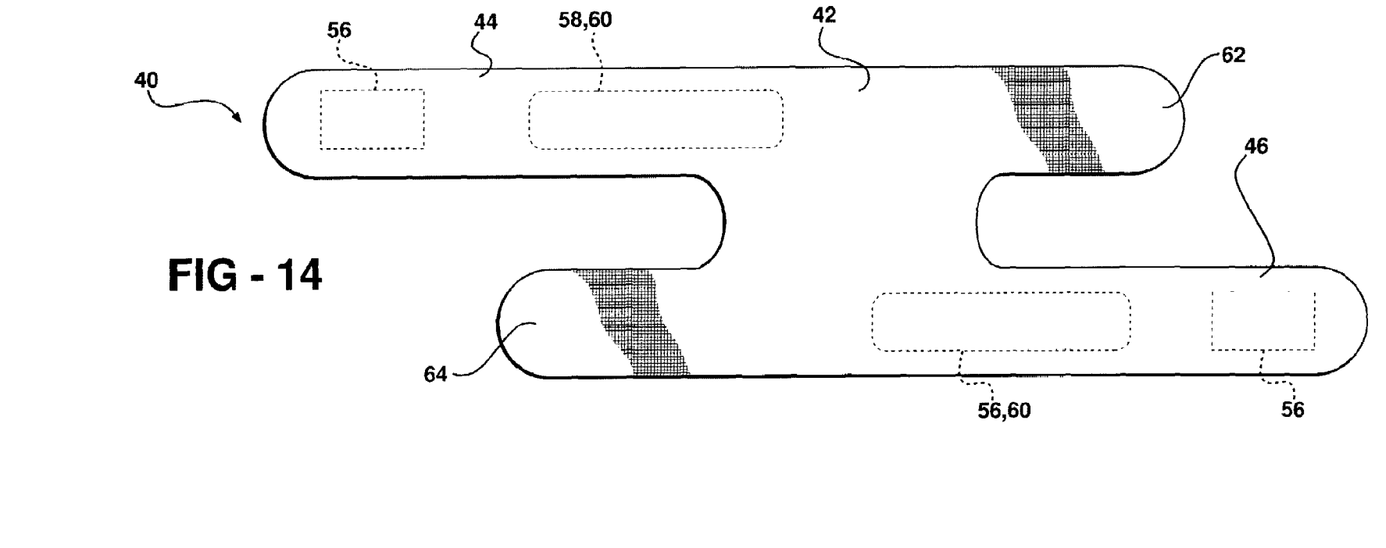
Figure 15:
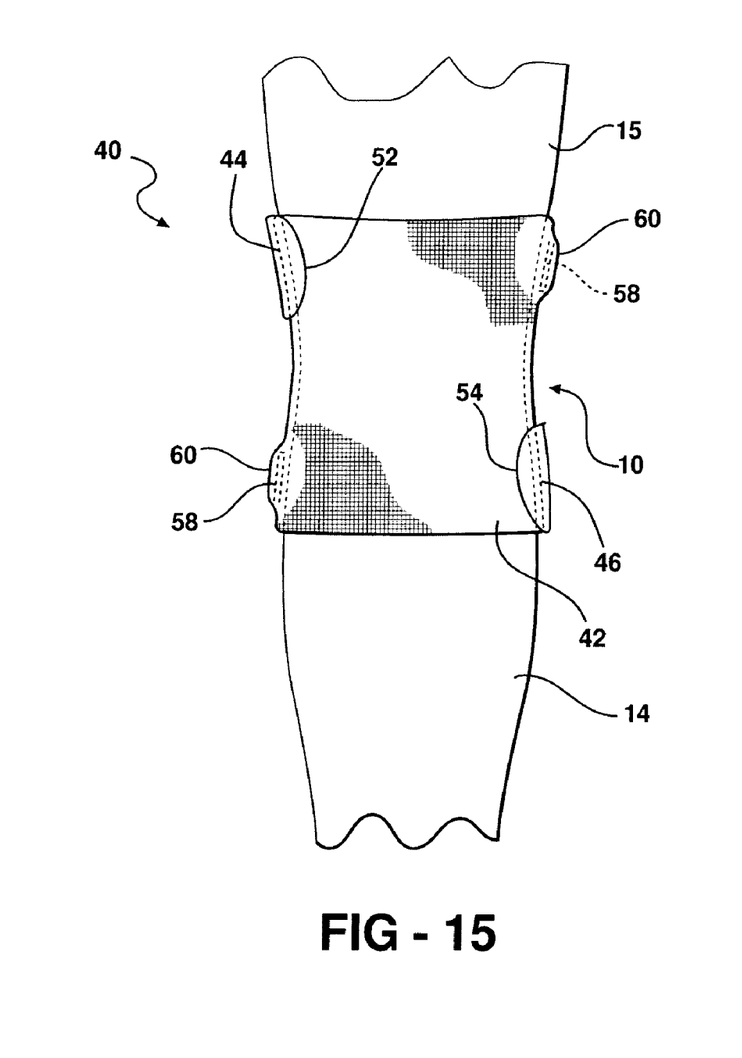
FIG. 15 is a view of the knee brace of FIGS. 13 and 14 shown mounted on the leg of a person viewed from the back of the knee.
Figure 16:
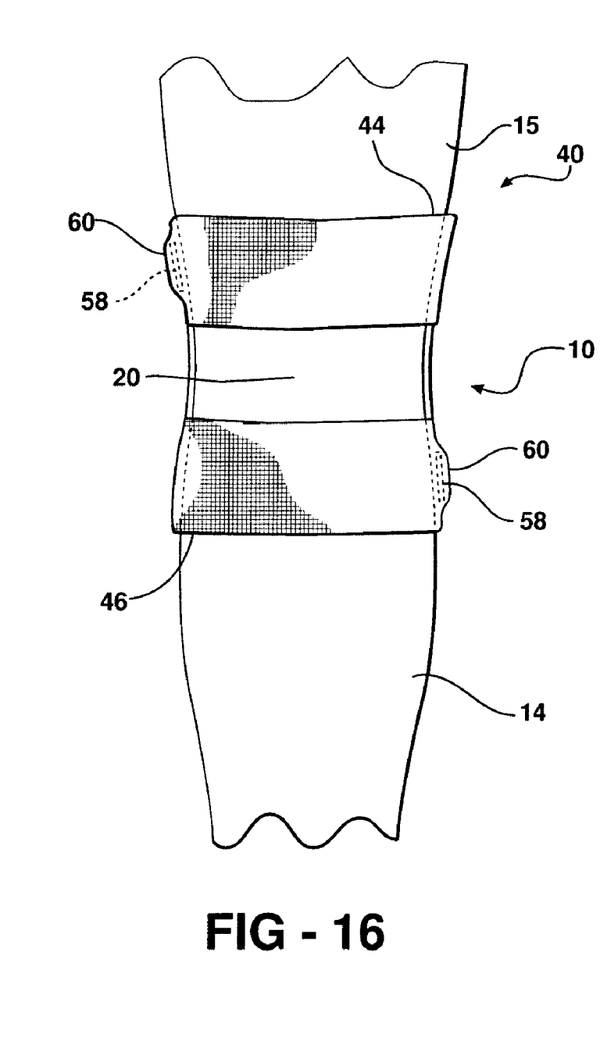
FIG. 16 is a view like FIG. 15 but of the front of the knee brace and leg.
Figure 20:
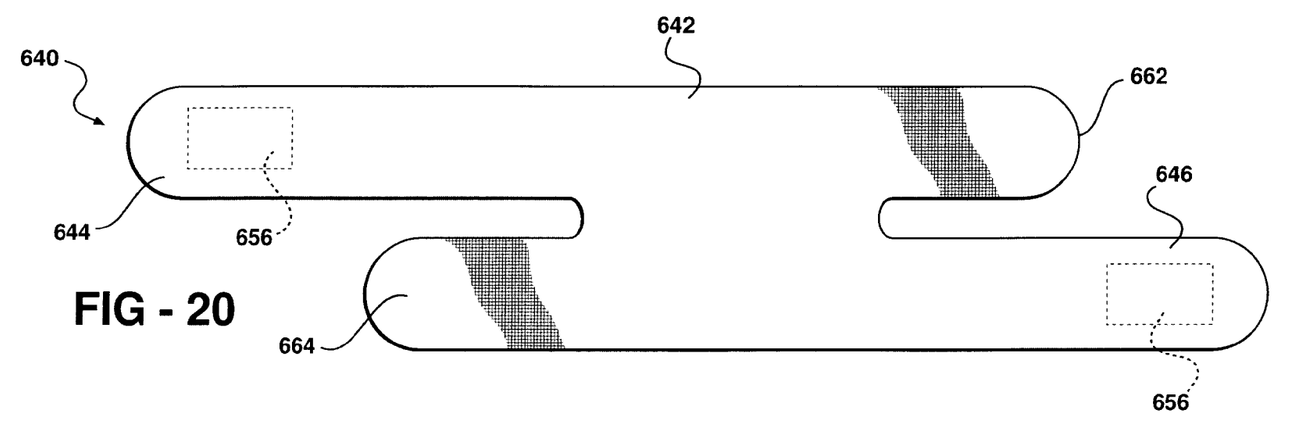
FIG. 20 illustrates a knee brace according to another embodiment of the invention.

The embodiment shown in FIGS. 20 and 21 is a wrap-type brace 640 similar to that shown in FIGS. 13 and 14, but lacking the stays 58 and stay pockets 60. The brace 640 includes a body 642 and straps 644, 662 and 646, 664 which extend from the body 642 to give the brace 640 an overall H-shape, but with the straps 644 and 646 being relatively longer than their opposing counterpart straps 662 and 664. It will be seen that the longer straps 644, 646 include a hook-type closure piece 656 which, when the brace 640 is wrapped about the leg as shown in FIG. 21, latches onto and is secured to the fabric of the respective shorter straps 662, 664. In addition, the upper strap 644 may be longer than the lower strap 646 to account for the larger diameter of the upper leg portion 15 relative to the lower leg portion 14.

Looking in particular at FIG. 21, it will be seen that the body 642 of the brace 640 is applied to the back of the knee and the straps 644, 662, 646, 664 are wrapped about the front of the leg. As viewed from the top of the leg looking down, the strap 644 is wrapped counter-clockwise about the upper leg portion 15 and attached to the corresponding shorter strap 662, whereas the lower strap 646 is wrapped clockwise and attached to the corresponding shorter strap 664. It is believed that this counter-wrapping of the straps 646 and 644 has the effect of exerting a torque on the underlying musculature, thus, resulting in laterally opposing forces $F_1$, $F_2$ on the leg above and below the knee joint 10, respectively. The forces $F_1$, $F_2$ are applied away from the patella 20, and thus, the patella 20 remains substantially free from any directly applied forces as a result of the knee brace 640. This results in counter-acting shear forces which has the effect of moving the upper leg 15 inwardly and the lower leg 14 outwardly to bring the upper and lower leg portions 15, 14 into proper axial alignment with one another to facilitate proper tracking of the patella 20 without acting directly on the patella 20. Since the patella 20 is not being acted on directly by the knee brace 640, the patella 20 is able to seek its natural motion within the aligned grooves 26, 28 of the femoral and tibial condyles 12, 22 without any undue influence from the knee brace 640. This results in proper functioning of the knee joint, without jeopardy of causing further damage to the joint. Thus, the counter-active shear forces have the effect of correcting the misalignment of the patello-femoral syndrome.

The amount of force $F_1$, $F_2$ applied by the straps 646, 644 can be adjusted by exerting more or less torque via the circumferential wrap force on the straps 646, 644. In comparison to the brace 40 of FIGS. 13 and 14, the magnitude of the resulting shear forces that can be generated will be less since the inclusion of the stays 24 has the effect of applying an increased load than that of the strap material, which enhances the force-applying capabilities of the brace when installed on the user's leg. In some cases, however, it is contemplated that users with only minor conditions of patello-femoral syndrome may only require a slight correction from the brace, and thus, the brace 640 of FIGS. 20 and 21 may be sufficient for such users. In addition, those that are using the brace 40 of FIGS. 13 and 14 may, over time, strengthen the muscles that support the knee such that the requirement or the inclusions of the stays 58 might diminish. As such, at some point the user can remove the stays 58 from their pockets 60 and use the brace 40 in similar fashion as that shown in FIGS. 20 and 21 to provide some support with shear force action, but less than that of the brace 40 fitted with the stays 58.

It is believed that the counter-wrapping of the straps 644, 646 (i.e., wrapping them in opposite directions about the leg above and below the knee joint) is one factor that induces counteracting torques which result in the lateral shear forces across the knee joint 10, wherein introduction of the stays 658 is another factor that, in the case of a wrap, adds to the counter-wrapping forces applied via the straps 644, 646.

The foregoing invention has been described in accordance with presently preferred embodiments, thus the description is exemplary rather than limiting in nature. Variations and modifications to the disclosed embodiment may become apparent to those skilled in the art, and thus, are within the scope of the invention. Accordingly, the scope of legal protection afforded this invention is defined by the following claims.

What is claimed is:

1. A method of manipulating the knee joint of a person's leg, comprising:
    obtaining a knee brace having a main body portion and at least two straps extending from the main body portion in opposite directions;
    positioning the knee brace on the person's leg with the main body portion positioned behind the knee joint and spaced from the patella of the person's knee joint;
    wrapping one of the straps in one direction around the front of the leg in a position spaced above the patella and securing a free end thereof operatively to the main body portion to hold the strap in place; and
    wrapping the other of the straps in the opposite direction around the front of the leg in a position spaced below the patella and securing a free end thereof operatively to the main body portion and including positioning a generally rigid stay to a lateral or medial side of the leg at a position spaced above the knee joint and securing it in place by one of the straps, and positioning another generally rigid stay to the opposite lateral or medial side of the leg at a position spaced below the knee joint and securing it in place by the other strap to impart opposite inwardly directed side loads to the leg above or below the knee joint and wherein the generally rigid stays are selected to be ones that extend lengthwise in the circumferential direction of the leg.

2. The method of claim 1 wherein the straps are secured in a manner that imparts a torque force to the leg across the knee joint with movement of the patella unimpaired by any direct application of force by the knee brace.

3. A knee brace for use by persons suffering from a patella femoral condition of a knee joint in which the femur and tibia of a leg of the person are misaligned either medially or laterally relative to a normal condition of alignment thereby causing abnormal patellar tracking along misaligned grooves of the femur and tibia and resulting in associated discomfort during movement of the knee joint, said knee brace comprising:
    a main body of the brace positionable behind the knee joint;
    an upper strap extending from an upper portion of said main body and wrappable in a first circumferential direction about an upper leg region of the person at a location spaced above the knee joint and secured at a distal end to the main body;
    a lower strap extending from a lower portion of the main body and wrappable about the lower leg region of the person at a location spaced below the knee joint and in the opposite circumferential direction as that of the upper strap such that the oppositely wrapped straps exert a collective torque force to the knee joint;
    an upper generally rigid member carried on said upper strap and a lower generally rigid member carried on said lower strap, said members being positioned along the straps such that when the straps are wrapped in place the upper member is pressed inwardly against one side only of the upper leg region at a location spaced above the knee joint and the lower member is pressed inwardly against the opposite side only of the lower leg region at a location spaced below the knee joint, such that a resultant lateral/medial directed shear force is exerted on the knee joint by the members; and
    wherein no portion of the knee brace applies a force directly on the patella.

4. The knee brace of claim 3 further comprising a pocket extending at least partially along one of said upper or lower straps for receipt of said generally rigid member to maintain said member along one of said sides of the knee joint.

5. The knee brace of claim 4 wherein said pocket is longer than said generally rigid member and provides space for adjustment of said generally rigid member along said side of the knee joint.

* * * * *

UNITED STATES PATENT AND TRADEMARK OFFICE
CERTIFICATE OF CORRECTION

PATENT NO. : 7,666,156 B2  Page 1 of 1
APPLICATION NO. : 11/466639
DATED : February 23, 2010
INVENTOR(S) : Alice M. Brown It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 245 days.

Signed and Sealed this

Seventh Day of December, 2010

David J. Kappos
*Director of the United States Patent and Trademark Office*